(12) United States Patent
Yoshiki et al.

(10) Patent No.: US 7,375,327 B2
(45) Date of Patent: May 20, 2008

(54) METHOD AND DEVICE FOR MEASURING QUANTITY OF WEAR

(75) Inventors: Masahiko Yoshiki, Kanagawa-ken (JP); Makoto Kato, Kanagawa-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 45 days.

(21) Appl. No.: 11/267,577

(22) Filed: Nov. 7, 2005

(65) Prior Publication Data

US 2006/0108545 A1 May 25, 2006

Related U.S. Application Data

(63) Continuation of application No. 10/413,286, filed on Apr. 15, 2003, now abandoned.

(30) Foreign Application Priority Data

Apr. 15, 2002 (JP) ............................. 2002-111785

(51) Int. Cl.
*G21K 7/00* (2006.01)
*G01N 23/227* (2006.01)
*G01N 23/00* (2006.01)

(52) U.S. Cl. ...................... 250/310; 250/305; 250/306; 250/307; 250/370.09; 250/492.3; 250/492.1; 250/492.2; 378/44; 378/45; 378/46; 378/50

(58) Field of Classification Search ................ 250/310; 378/50
See application file for complete search history.

(56) References Cited

U.S. PATENT DOCUMENTS 4,597,093 A * 6/1986 Fischer ........................ 378/50

(Continued)

FOREIGN PATENT DOCUMENTS

JP 2-108949 4/1990

(Continued)

OTHER PUBLICATIONS

P. Lemoine, et al., J.Vac. Sci. Technol. A, vol. 17, No. 1, pp. 176-182, "Continuity and Topography of Ultrathin Diamond-Like Carbon Films Characterized by Scanning Electron Microscopy/Energy Dispersive X-Ray Analysis and Atomic Force Microscopy," Jan./Feb. 1999.

(Continued)

*Primary Examiner*—David Vanore
*Assistant Examiner*—Bernard Souw
(74) *Attorney, Agent, or Firm*—Oblon, Spivak, McClelland, Maier & Neustadt, P.C.

(57) ABSTRACT

A method and device to accurately obtain very small quantity of wear of the order of nanometers of a protective film on the surface of a sliding member. A quantity of wear on the surface of a measurement sample including a base and a coating layer is measured by making a spectrum of the surface elements in a reference sample using a surface-element analysis device which analyzes elements on the surface of a substance from an energy spectrum of charged particles obtained by applying excited ionization radiation on the reference sample equivalent to the measurement and by measuring charged particles generated from the surface of the substance. A step of obtaining signal intensity ratios of plural elements from the spectrum is repeated a plurality of times while the surface of the reference sample is being etched and calibration curves which indicate a distribution of the signal intensity ratios of the plural elements in the reference sample are made. Subsequently, an energy spectrum of charged particles from the surface of the measurement sample is measured, signal intensity ratios of specific elements are calculated and compared with the calibration curves to determine a quantity of wear of the measurement sample.

14 Claims, 6 Drawing Sheets

U.S. PATENT DOCUMENTS

| | | | | |
|---|---|---|---|---|
| 4,799,246 | A * | 1/1989 | Fischer | 378/50 |
| 5,061,562 | A * | 10/1991 | Yamanaka et al. | 428/408 |
| 5,750,747 | A | 5/1998 | Furutani et al. | |
| 5,776,602 | A | 7/1998 | Ueda et al. | |
| 5,982,847 | A * | 11/1999 | Nelson | 378/47 |
| 6,110,330 | A | 8/2000 | Lin et al. | |
| 6,512,810 | B1 * | 1/2003 | Haszler et al. | 378/45 |
| 6,558,822 | B2 * | 5/2003 | Nagasaka et al. | 428/700 |
| 6,611,576 | B1 * | 8/2003 | Besser et al. | 378/48 |
| 6,631,177 | B1 * | 10/2003 | Haszler et al. | 378/50 |
| 6,668,039 | B2 * | 12/2003 | Shepard et al. | 378/47 |
| 6,859,517 | B2 * | 2/2005 | Wilson et al. | 378/47 |
| 7,184,515 | B2 * | 2/2007 | Wilson | 378/47 |
| 2001/0038894 | A1 | 11/2001 | Komada | |
| 2002/0017235 | A1 * | 2/2002 | Nagasaka et al. | 117/106 |
| 2003/0094085 | A1 | 5/2003 | Ueda et al. | |
| 2003/0128805 | A1 * | 7/2003 | Shepard et al. | 378/47 |
| 2004/0011957 | A1 * | 1/2004 | Yoshiki et al. | 250/307 |
| 2006/0011865 | A1 * | 1/2006 | Migeon et al. | 250/492.3 |
| 2006/0067465 | A1 * | 3/2006 | Wilson | 378/47 |
| 2006/0108545 | A1 * | 5/2006 | Yoshiki et al. | 250/492.21 |
| 2006/0223718 | A1 * | 10/2006 | Bastien et al. | 508/365 |

FOREIGN PATENT DOCUMENTS

JP      2001-343227      12/2001

OTHER PUBLICATIONS

R.H..Wang, et al., IEEE Transactions on Magnetics, vol. 38, No. 5, pp. 2132-2134, "Head-Disk Interface Considerations at 10-nm Flying Height," Sep. 2002.

Royston Paynter, "Basic principles of x-ray photoelectron spectroscopy," dated Jan. 14, 1998, http://www.inrsener uquebec.ca/commerce/xps-tech.html.

"Auger Electron Spectroscopy," dated Apr. 5, 1997, http://www.chem.qmw.ac.uk/surfaces/scc/scat5-2.htr.

* cited by examiner

METHOD AND DEVICE FOR MEASURING QUANTITY OF WEAR

CROSS REFERENCE TO RELATED APLICATION

This application is a Continuation of Application Ser. No. 10/413,286 filed Apr. 15, 2003 and claims the benefit of priority from the prior Japanese Patent Application No. 2002-111785, filed Apr. 15, 2002; the entire contents of which are incorporated herein by reference.

BACKGROUND OF THE INVENTION

1. Field of the Invention

The present invention relates to a method and a device, which measure a quantity of wear on a protective film formed on a surface of a sliding member, especially a very small quantity of wear of the order of nanometers in order to improve the wear resistance of a sliding member on which wear is caused by contact with other members.

2. Description of the Related Art

When two or more members such as a bearing, a contact part of a switch, a head and a disk in a hard disk drive, are moving (sliding) under a state that the two or more members are contacting with each other, or are discontinuously contacting with each other, a wear resisting protective film of diamond-like carbon and the like has been formed on the surface of the member in order to prevent damages of the member and an increase in friction resistance, which are caused by wear. In such a case, a method which measures a wear quantity of the protective film has been required for optimized designing of a kind and a thickness of the protective film and for prediction of wear life indicating a period to disappearance of the protective film due to the wear.

The simplest method has been a method in which a prism, a pin, or the like is put into contact with a sliding member having a protective film formed thereon and wear caused by relative motion therebetween in a back and forth manner is observed. Though the quantity of wear may be obtained from the area of the worn part or the displacement of the pin, the quantity of wear of at least less than the order of microns may not be measured by the above method. Also, the above method is not appropriate for measurement of a protective film with a thickness of equal to or less than 10 mm which has been used for the thickness of a hard disk drive and the like, for sliding conditions are largely different from environments, in which the protective film has been really used, to cause problems that an effective hardness of the protective film, or a wear mechanism itself is different from real conditions.

Another method which can be used for measurement of a member which has the same structure and which is worn in the same environments with those of real use is a method using an optical shape evaluation device. In the above method, a quantity of wear is obtained as a change in the shape of a wear surface and the quantity of wear may be obtained with an accuracy of equal to or less than 1 nm when the wear is locally occurred, or when an originally convex place is worn out. However, measurement with a high accuracy cannot be expected when the wear surface is approximately parallel to the original surface, or when individual differences in the irregular shapes on the wear surface are large.

Separately from the above-described measurement method by use of changes in the shape, a method which measures the quantity of wear from the thickness of the protective film after sliding has been considered in the case of a protective film with a thin thickness. When the above method is used, the quantity of wear may be measured with the same accuracy as that of the film-thickness measurement, even when the wear surface is parallel to the original surface, and even if there are some individual differences in the surface shapes. Especially, an X-ray photoelectric spectrum analysis method (XPS) in which the X ray is applied on a sample and photoelectrons are detected, the Auger electron spectroscopy (AES) in which an electron beam is applied on a sample and Auger electrons are detected, and the like may be applied for the above-described measurement of a film thickness of approximately 10 nm.

A method in which a film thickness is obtained by measuring ratios between signals of elements embedded in the film and signals of elements included in the base are measured, and by using a theoretical formula indicating a relation between the above ratios and the film thicknesses has been generally applied for the film-thickness measurement using the X-ray photoelectric spectrum method. Such a formula is usually based on a layer structure with a steep interface and parameters such as a mean free path of photoelectrons depending on materials are required to be obtained beforehand by measuring a reference sample with a known film thickness. Since it is difficult to guarantee accuracy of equal to or less than 1 nm by reasoning that approximation or assumption is included in the above theoretical formula as described above, a reference sample and a measurement sample are not strictly the same, and the like, the above formula is not sufficient for measurement of a very small quantity of wear, that is, a reduced film-thickness.

On the other hand, when a film thickness is measured using the Auger electron spectroscopy, a method in which a film thickness is obtained from the sputter time to an appearance of an element embedded in the film, or to a disappearance of the element embedded in the base after measurement of a depth-direction distribution of the element together with sputter etching has been generally used. A sputter etching rate which is required for conversion of sputter time to a film thickness is obtained by measurement in which a reference sample with a known film thickness is measured beforehand, or by measurement of the depth of a sputter etching part with a stylus-type level sensor. The above method is also unsuitable for wear measurement with high accuracy, for a reference sample and a measurement one are not strictly the same, and fluctuations in the sputter etching rates between measurements of both of the samples are directly reflected on the changes in the film thickness.

As described above, the measurement of very small wear of the order of nanometers has been difficult by conventional methods.

SUMMARY OF THE INVENTION

The present invention has solved problems of conventional techniques which has been described above and its object is to provide a method and a device for measuring very small wear, which can measure very small wear of the order of nanometers for a protective film on the surface of a sliding member.

A first aspect of the present invention provides a wear measurement method of measuring a quantity of wear on the surface of a measurement sample formed with a surface layer on a base material, comprising:

a reference-sample detection step of repeatedly recording a ratio between a signal intensity caused by an element in a base layer of the reference sample and a signal intensity caused by an element in the surface layer of the reference sample, which are obtained by etching a reference sample with the same layer structure as that of the measurement sample before substantial wear in the direction of the film thickness for preliminary wear and by applying excited ionization radiation on the reference sample during being etched and by detecting charged particles generated from the reference sample, and obtaining a relation between the quantities of preliminary wear and the ratios of the reference sample;

a measurement-sample detection step of detecting ratios between signal intensities caused by elements in the base layer of the measurement sample and signal intensities caused by elements in the surface layer of the measurement sample, which are obtained by applying the excited ionization radiation on the measurement sample after surface wear and by detecting charged particles generated from the measurement sample; and a step of obtaining positional information on the surface of the measurement sample after wear by comparing the relation obtained in the reference sample detection step with the ratios detected in the measurement sample detection step.

A second aspect of the present invention provides a wear measurement device comprising:

charged particle measurement means for applying excited ionization radiation on a sample and measuring charged particles generated from the surface of the sample;

means for generating an energy spectrum of the charged particles based on an output signal from the charged particle measurement means;

means for calculating signal intensities of plural elements forming the sample from the energy spectrum of the charged particles and calculating signal intensity ratios from the signal intensities of the plural elements;

means for making and recording calibration curves indicating relations between the signal intensity ratios of the plural elements and depth-positional information on the sample for which the energy spectrum of charged particles has been observed;

means for measuring values of the signal intensity ratios of the plural elements calculated from the energy spectrum of charged particles for the measurement sample; and means for calculating the quantity of wear for the measurement sample from the values of the signal intensity ratios of the plural elements for the measurement sample and data of the calibration curves.

DESCRIPTION OF THE PREFERRED EMBODIMENTS

Hereinafter, a principle of a measurement method according to the present invention will be explained.

In the wear measurement method according to the present invention, an intensity ratio between a signal from a surface layer and that from a base layer, which are obtained by using an analytical method such as an X-ray photoelectron spectroscopy or Auger electron spectroscopy, is converted to a quantity of wear not by a theoretical formula but by comparison with depth-direction changes in the intensity ratios obtained by real measurement, that is, but by comparison with the depth-direction distribution.

Figure 1A:
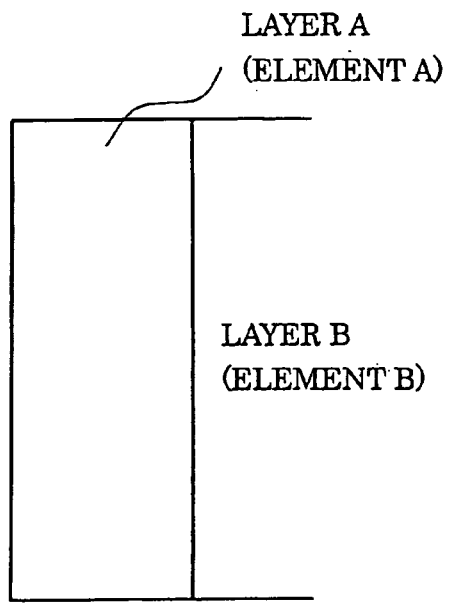
FIGS. 1A to 1C show a schematic view showing a principle of the present invention.
Figure 1B:
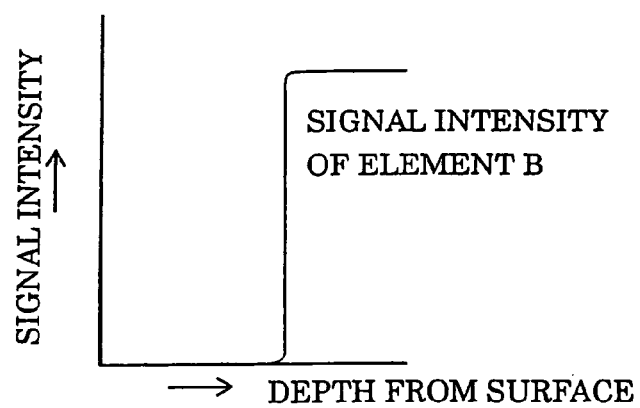
Figure 1C:
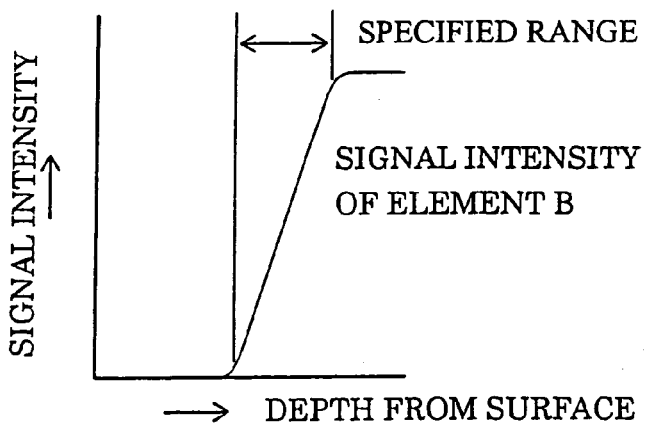

Explanation will be made, referring to FIG. 1 showing the principle of the present invention. FIG. 1A shows a schematic view of one example of a sample with regard to which a quantity of wear is measured according to the present invention. In FIG. 1A, a sample with two layers will be given as one example, and it is assumed that the sample comprises a surface layer A as a surface to be worn and a base layer B as a base, while the surface layer A contains an element A and the base layer B includes an element B. With regard to the sample, excited ionization radiation is applied on the surface of the sample sequentially from the surface layer according to the X-ray photoelectric spectrum analysis method (XPS) or Auger electron spectroscopy (AES), and charged particles generated from the surface of the sample are measured, an energy distribution spectrum of the charged particles is made, and signal intensity is measured for an object element from the energy spectrum of the charged particles. Thereafter, the surface layer is etched according to a method such as sputtering, the energy spectrum of charged particles is further made for a new surface, signal intensities are measured for an object element, the measured results are plotted against distances from the initial surface of the sample, and then, a graph such as FIG. 1B may be obtained. In the diagram of FIG. 1B, the signal intensities are plotted against the depth from the surface for the element B included in the base layer B. The above diagram shows that the intensities clearly show a drastic change at the interface between the surface layer A and the base layer B and that the energy spectrum of the charged particles has been ideally measured. But, actually, there is, as shown in FIG. 1C, a gradually increasing tendency which is caused by a dull rise of a signal at the interface between the surface layer A and the base layer B, for the element A in the surface layer A and the element B in the base layer B are transferred to each other to cause a disturbance on the interface, or transfers of elements are generated by sputtering when the sample is manufactured. The actual diagram shown above is reproduced in an extremely precise manner if the manufacturing process of the sample and the observation conditions are the same. It is found as shown in FIG. 1C that a depth from the surface corresponding to a signal intensity of a specific element is obtained during the process between the rise and the saturation of the curve in the diagram if the intensity is acquired.

As described above, after the energy spectrum of charged particles on the surface of a worn sample is measured and the signal intensity of a specific element has been obtained, a depth from the surface corresponding to the intensity, that is, the quantity of wear can be determined by comparing with a calibration curve previously obtained for a reference sample.

While the absolute value of the signal intensity of a specific element can be converted to the quantity of wear in the graph shown in FIG. 1C, it is difficult to say that the converted quantity of the wear is fully reliable, for the absolute value of the signal intensity is sensitive to observation conditions of the energy spectrum of charged particles and the absolute value of the signal intensity changes greatly even by the small change. Accordingly, if signal intensities of two or more kinds of elements are measured and the signal intensity ratios therebetween are calculated, changes caused by observation conditions may be reduced and reliable values can be obtained.

Figure 5A:
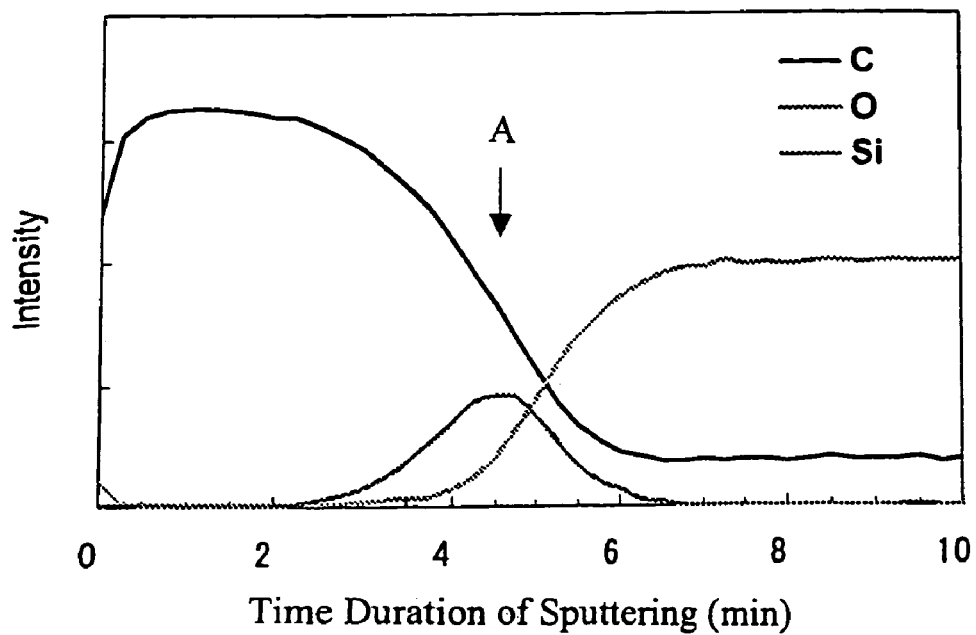
FIG. 5A is a view showing signal intensities of a reference sample according to the example of the present invention.
Figure 5B:
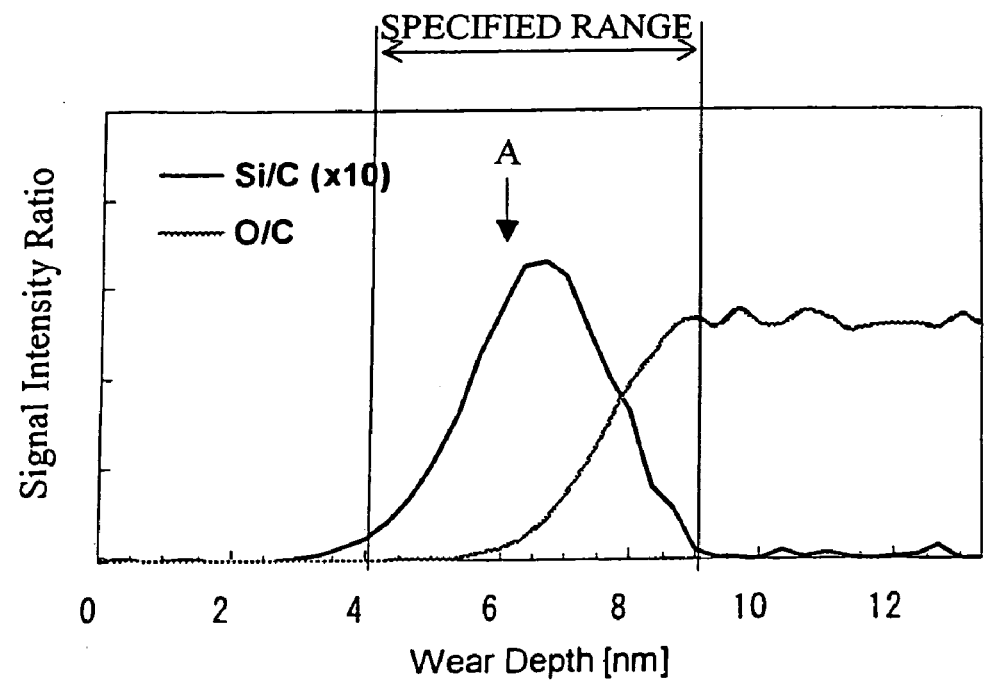
FIG. 5B is a view showing examples of depth-direction profiles for signal intensity ratios according to the example of the present invention.

Moreover, when a measurement sample has a configuration with three or more layers, the signal intensities of three or more object elements are measured from the energy spectrum of the charged particles and two or more calibration curves may be made. According to the above method, the quantity of wear can be decided even for an area in which the quantity can not be decided by a single calibration curve, as shown in FIG. 5B.

As described above, the quantity of the wear may be obtained with high accuracy and without effects of approximation or assumption, which is a key factor in a theoretical formula, according to the method of the present invention. Moreover, generation of errors caused by differences in the film thickness and the composition between the measurement sample and the reference sample may be prevented by measurement of the intensity ratios for the depth-direction distribution with the same analytical method as that of the measurement sample with regard to the reference sample with the surface layer which is of the same protective film as that of the sample to be evaluated.

When there is, in the above-described depth-direction distribution, a depth range within which a signal from the base layer is not detected, that is, a depth range within which the intensity ratio becomes constant, the intensity ratio may not be converted to the quantity of the wear if the quantity of the wear on the measurement sample is within said depth range. In such a case, the intensity ratio may be converted to the quantity of the wear by sputter etching beforehand the coating layer, which is of the protective film of the measurement sample, into the depth range within which the intensity ratio changes. A real quantity of the wear may be obtained from the difference between the apparent quantity of the wear (real quantity of wear and etched quantity) which has been obtained as described above and a sputter etching quantity which is obtained by multiplication of a sputter etching rate, which has been obtained beforehand, by a sputter time.

However, in the above-described method using the sputter etching, there is a possibility that the measurement accuracy is reduced by deviation of the sputter etching rate from the value obtained beforehand, which is caused by fluctuation in the sputter etching conditions. However, when there is, in the measurement sample, a wear area (an area in which wear may be caused, for example, by sliding) and a non-wear area (an area in which there is not worn, for example, due to no possibility of sliding), the real quantity of the wear for the area to be evaluated may be accurately obtained from the difference in the apparent quantity of the wear between two areas. That is, the effects of fluctuation in the sputter etching rate may be suppressed and the very small quantity of wear may be evaluated with high accuracy by setting the area, in which the protective film is not worn, as a reference level.

Hereinafter, a sample, a method and a device for measuring a quantity of wear will be explained one after another as one embodiment according to the present invention.

Sample

A component, for which a wear resisting protective film of diamond-like carbon and the like is formed on its surface in order to prevent damages of the component and an increase in friction resistance, which are caused, as described above, by wear due to sliding when two or more components such as a bearing, a contact part of a switch, a head and a disk in a hard disk drive are contacting with each other or due to discontinuous contact between the two or more components, is suitable for measurement of a quantity of wear on a sample by application of the present invention. Moreover, when an adhesive property between the material of the base and the protective film is not good, the invention may be also applied to a structure formed with a material layer by which the base material is adhered to the protective film. In such a structure, it is preferable that the film thickness is of approximately 50 nm or less for the adhesion layer and the protective film. When these film thicknesses exceed the above range, the surface protective layer is required to be etched and to be removed near to the interface between the surface protective film and the base layer which is contacting with the above protective film, or the adhesion layer. But errors in the thickness of the film removed by etching become large, and accordingly, the errors in measured values of the quantity of wear to be measured become large so that the measured values are not practically used. Also, the thickness of the surface protective layer has no special limitation and it is possible to measure wear with a thickness of up to approximately 0.1 nm with sufficient accuracy.

The present invention is suitable for exact measurement of extremely small wear and best, for example, for measurement of wear with a depth of to approximately 5 nm. Though it is also possible to measure wear with a thickness of exceeding 10 nm, such a thickness of wear is within an area in which measurement can be realized by another simpler measurement means and it is preferable to measure a sample with wear having a thickness of 5 nm or less in order to make the most of the feature of the present invention.

A sample to which the present invention is applied comprises as described above: a base; a coating which protects the surface of the base; and, if required, an adhesion layer which is arranged at the interface between the base and the coating, and the interfaces between the above layers are preferably flat. Also, the above layers are required to contain elements which are different from each other. Assuming that the above different elements are used as an observation element, it is preferable that each of the above observation elements is a principal component element for each layer. When the portion of each observation element is small in each layer signal intensities calculated from the observed charged particle energy spectrum become small to cause larger errors.

In the present invention, a measurement sample and a reference sample are used for measuring a quantity of wear, and it is preferable that conditions, such as an element composition, a layer configuration and a thickness of the layer for the above measurement sample are equal to those of the reference sample. Therefor, it is preferable that the reference sample is formed according to the same steps as those of the measurement sample.

Measurement Method

The method of measuring a quantity of wear according to the present invention will be explained.

In this measurement method, an energy spectrum of charged particles from a plurality of layers is observed in the depth direction from the surface layer by an ultimate analysis technique with regard to a reference sample, processing which makes calibration curves indicating a relation between signal intensity ratios and positional information of specific elements in the depth direction is executed, an energy spectrum of charged particles is observed for a real measurement sample, signal intensities are measured from the energy spectrum of the charged particles for specific elements, positional information in the depth direction is determined from the above-described calibration curve, and a quantity of wear is obtained.

In this method, a measurement sample for which a quantity of wear is measured and a reference sample which has the same element composition and the same layer configuration and is manufactured by the same manufacturing method as those of the measurement sample are prepared. It is preferable that the above reference sample is formed in the same steps, and at the same time, on the same member which is not subject to wear, as those of the measurement sample.

In the first place, calibration curves indicating relations between the quantity of wear and the signal intensity ratios of specific elements are made, using the reference sample.

Figure 4A:
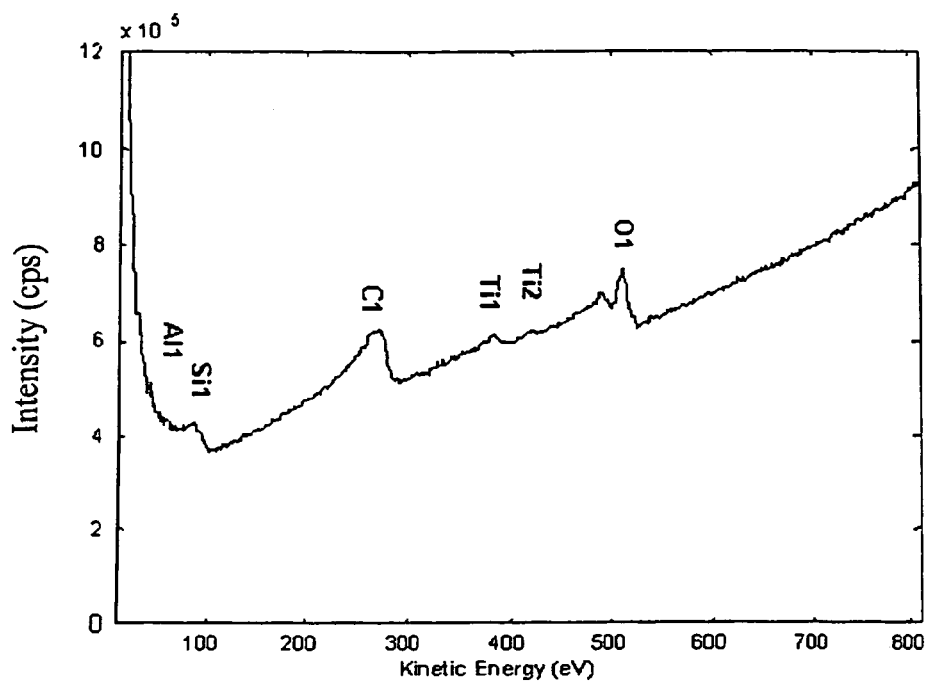
FIG. 4A is a view showing one example of an Auger electronic spectrum analysis according to the example of the present invention.
Figure 4B:
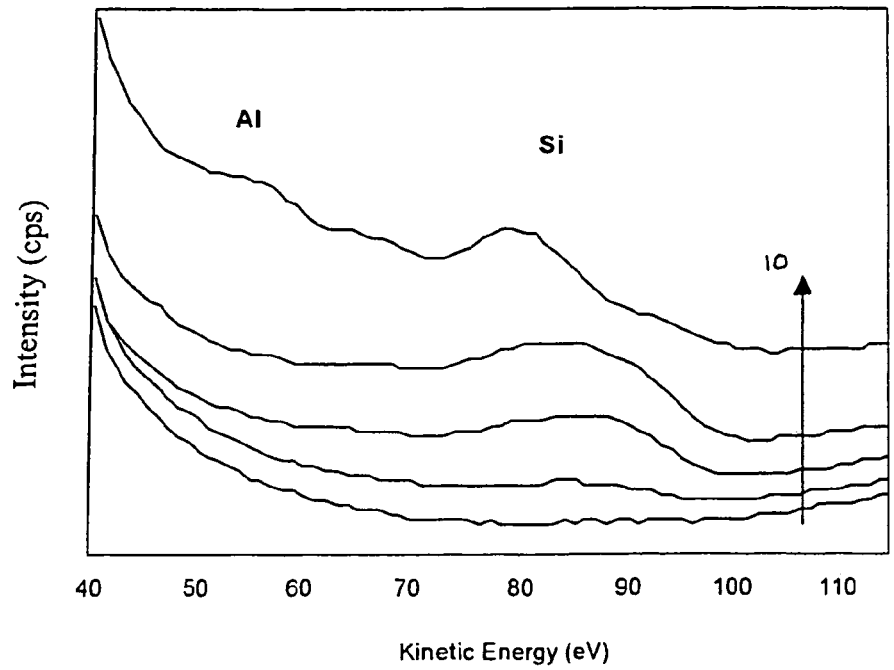
FIG. 4B is a view showing changes in energy spectrums of charged particles due to quantities of wear according to the example of the present invention.

That is, excited ionization radiation is applied on the surface of the sample according to the X-ray photoelectric spectrum analysis method (XPS) or Auger electron spectroscopy (AES), and charged particles generated from the surface of the sample are measured to make an energy spectrum of the charged particles. FIG. 4 shows one example of the energy spectrum of the charged particles obtained by Auger electron spectroscopy. FIG. 4A shows measurement results in an area up to a kinetic energy of 800 eV, and FIG. 4B shows superimposed results of measurements which have been conducted in an area up to a kinetic energy of approximately 115 eV for five samples different in the quantity of the wear.

In the energy spectrum of the charged particles in FIG. 4, observed peaks correspond to elements, respectively, and elements are specified from the kinetic energy at each peak, respectively, to realize measurements of signal intensities. There have been the following methods which determine the signal intensities: a method of differentiating an energy spectrum of charged particles to measure a peak-to-peak intensity; a method in which it is assumed that a signal intensity is a peak area excluding a background; and a method in which a signal intensity is assumed to be a peak height of the energy spectrum of the charged particles after smoothing processing of the above energy spectrum. All of the above methods have been a well-known technique, as described in documents such as "Auger electron spectroscopy", edited by the Surface Science Society of Japan and published by Maruzen Co., Ltd. in 2001). It is preferable in the present invention that the signal intensity is measured from the peak height of the energy spectrum of the charged particles after smoothing processing, as described in the above third method, for processing is easy when the signal intensity possibly is zero in the sample according to the present invention and the accuracy of measurement of the quantity of wear becomes better due to great changes in the signal intensity in the depth direction.

Then, signal intensity ratios between the specific elements are calculated from pieces of the data on the signal intensities of the elements as obtained above and are stored as values of the signal intensity ratios between the specific elements, which correspond to the depths from the surface in the measured reference sample.

Subsequently, the above reference sample is etched to a predetermined thickness of the surface and a signal intensity ratio of the specific elements is measured for the newly-generated surface by equivalent means to that of the above-described step. Then, the obtained value is stored in the same manner as that of the above case as data of the signal intensity ratio of the specific element, which corresponds to the etched depth, that is, to the distance from the surface of the sample. The above steps are repeated two or more times to make a graph indicating relations between the signal intensity ratios and the quantities of the wear.

The above steps are shown in drawings. That is, FIG. 5A shows the signal intensities of the specific elements among elements forming the sample, which are obtained from the energy spectrum of the charged particles in FIG. 4. In FIG. 5A, the horizontal axis indicates sputtered time in the case where the reference sample is etched by sputtering. The sputter time is proportional to the depth from the surface of the sample under the assumption that the sputtering rate is constant. Accordingly, the sputter time can be easily converted to the depth information.

Then, the graphs, that is, the calibration curves, which indicate relations between the signal intensity ratios of the specific elements and the quantities of wear as shown in FIG. 5B, are made from pieces of the data on the sputter time and the signal intensities of the specific elements, which are shown in FIG. 5A. After the sputter time in the horizontal axis of FIG. 5A is converted to the distance from the surface and the signal intensity ratios of the specific elements are calculated, the above calibration curves may be made by plotting the calculated results.

Subsequently, in the same manner as that of the above-described reference sample, excited ionization radiation is applied on the surface of the measurement sample, which is an object sample for measurement of a quantity of wear, charged particles generated from the surface of the above-described measurement sample are measured to make the energy spectrum of the charged particles, and the signal intensity ratios between the above-described two or more specific elements are calculated from the above-described energy spectrum of the charged particles. The obtained values of the signal intensity ratios of the specific elements are compared with the above-described calibration curves to determine the quantity of the wear of the above-described measurement sample.

In the above-described explanation, graphs such as the energy spectrum of the charged particles, relations between etched time and signal intensities, and calibration curves have been made with regard to a sample for easier explanation, but it is really preferable that the processing is electronically done, using an electronic computer and the like.

Then, a method which is used for measurement of a quantity of wear of a measurement sample when the quantity of the wear is small and a signal intensity ratio within the decidable range shown in FIG. 1C is not observed in the energy spectrum of the charged particles from the surface of the measurement sample will be explained.

According to this method, the surface of a measurement sample with a small quantity of wear is etched by sputtering and the like by a predetermined thickness, an energy spectrum of charged particles is measured for the above new surface, a corresponding depth is obtained from calibration curves, using the values of the signal intensity ratios of specific elements which have been obtained from the above energy spectrum of charged particles, and the etched thickness is subtracted to determine the quantity of wear. In such a case, even an area with no wear is simultaneously etched when the measurement sample is etched by sputtering, and the area is assumed to be a standard to calculate the quantity of wear, for the accuracy in measurement of the quantity of wear is effected by the accuracy of a sputtering quantity. That is, when it is assumed that a calculated value of the quantity of wear for the measurement sample is D and the quantity of wear at a reference point is R, the real quantity of wear for the measurement sample becomes D–R. According to the above method, a measured value may be obtained with high accuracy, independent of changes in etching conditions.

Wear Measurement Device

A wear measurement device according to the present invention comprises: energy spectrum of the charged particles and calculating signal intensity ratios from the signal intensities of the plural elements; means for making and recording calibration curves indicating relations between the signal intensity ratios of the plural elements and depth-positional information on the sample for which the energy spectrum of charged particles has been observed; means for measuring values of the signal intensity ratios of the plural elements calculated from the energy spectrum of charged particles for the measurement sample; and means for calculating the quantity of wear for the measurement sample from the values of the signal intensity ratios of the plural elements for the measurement sample and data of the calibration curves.

Figure 7:
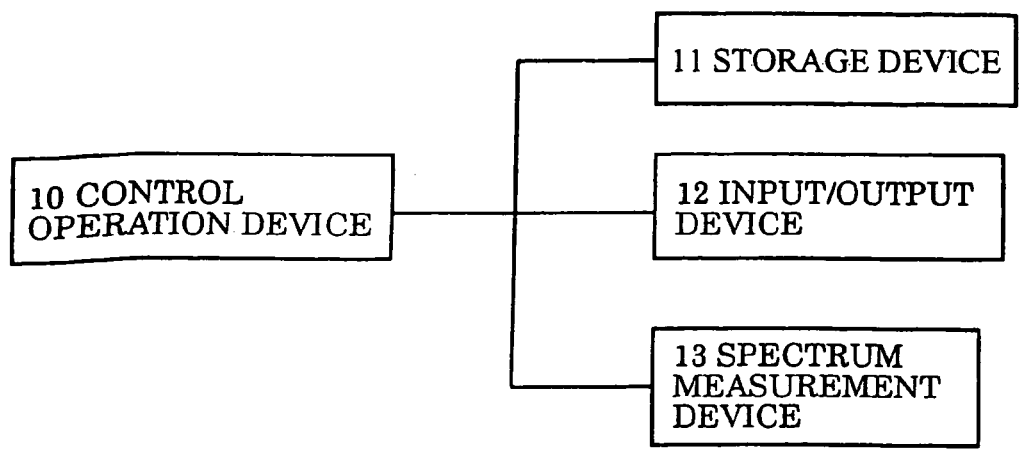
FIG. 7 is a schematic view of a wear measurement device according to the present invention.

The wear measurement device according to the present invention is specifically shown in FIG. 7.

In FIG. 7, 10 is a control operation device which controls the whole parts of the wear measurement device according to the invention and executes predetermined operations, and a so-called electronic computer may be used as the device 10. A charged particle energy spectrum measurement device 13, a storage device 11, and an input/output device 12 are connected to the control operation device.

The charged particle energy spectrum measurement device 13 is a device which measures an energy spectrum of charged particles indicating energy distribution of the charged particles by applying excited ionization radiation on the surface of a sample and measuring charged particles generated from the surface of the above-described sample. Commercially available devices adopting the X-ray photoelectric spectrum analysis method (XPS) or Auger electron spectroscopy (AES) may be used as the measurement device 13 as described above. The energy spectrum of charged particle which is an output signal from the above device is input to the control operation device 10 as a digital signal.

This input data on the energy spectrum of the charged particles is input to the storage device 11 and stored therein in relation with conditions for the measured charged particle energy spectrum, that is, distinction of the energy spectrum of the charge particles between the reference sample and the measurement sample, or the positional information on the measured surface, that is, information on the film thickness which has been removed by etching.

Then, pieces of the data of the energy spectrum of the charged particles for plural reference samples which have been stored in the above-described storage device 11 are transferred to the control operation device 10 and signal intensities of specific elements are calculated according to an algorithm by which a method determining the signal intensities of the specific elements, such as a method by which an energy spectrum of charged particles is differentiated and a peak-to-peak intensity is measured; a method in which it is assumed that the signal intensity is a peak area excluding the background; and a method in which the signal intensity is assumed to be the peak height of the energy spectrum of the charged particles after smoothing processing of the above energy spectrum of charged particles is realized. Then, calibration curves are made, based on the above signal intensities of the specific elements. Though the above calibration curves are made in the form of a graph as shown in FIG. 5B, the above curves can be also made in the form of a table, such as a conversion table in which quantities of wear are in relation with values of signal intensity ratios, on an electronic computer. In addition, the above calibration curves may be stored as an approximate function when the above curves in the diagram may be approximated by the function.

In FIG. 7, 12 is the input/output device which is used for input of measurement conditions and the like and for output of measurement results, and is realized by an image and character display such as a keyboard and a CRT of an electronic computer.

Also, the wear measurement device according to the present invention may be made by combination of a general-purpose electronic computer and a general-purpose spectrum analysis device, and the function as the wear measurement device according to the invention may be realized by software. On the other hand, each function may be realized by pieces of individual special-purpose hardware which are controlled by a special control device.

EXAMPLE

Hereinafter, an example according to the present invention, in which the quantity of wear of a head protective film for a hard disk drive was measured using the Auger electron spectroscopy, will be explained, referring to FIG. 2 through FIG. 6.

Figure 2:
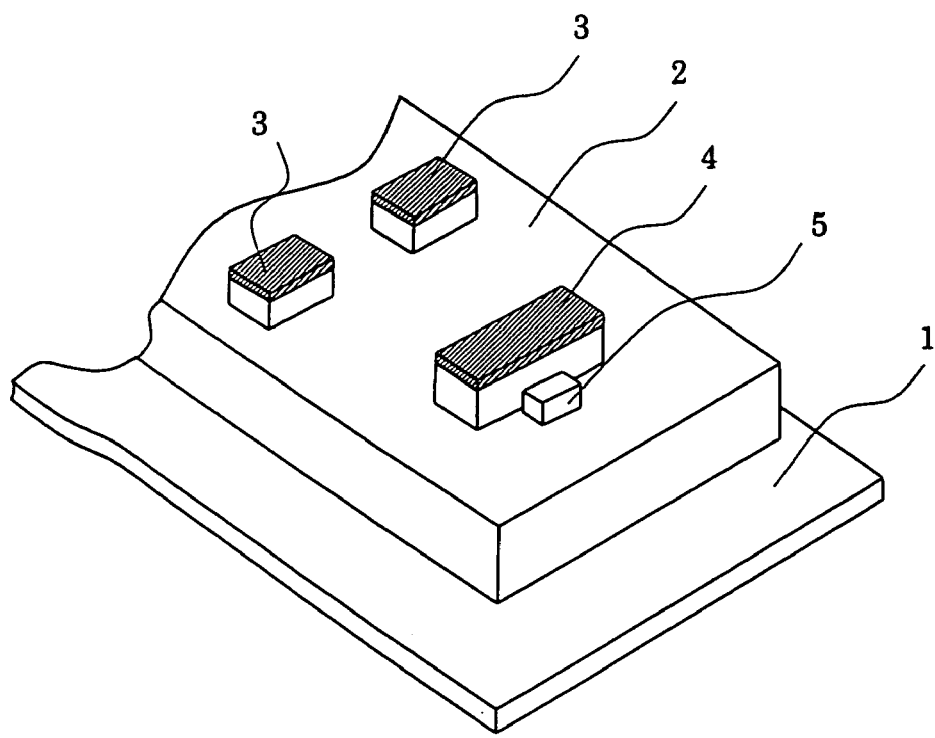
FIG. 2 is a schematic view showing a structure near a head of a hard disk drive according to an example of the present invention.
Figure 3:
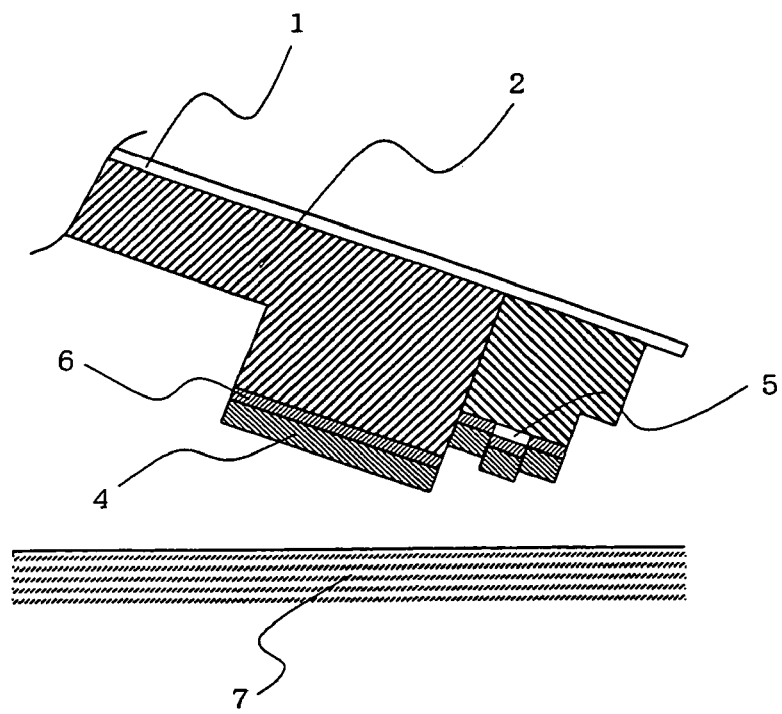
FIG. 3 is a schematic sectional view showing an appearance near the head of the hard disk drive according to the example of the present invention under operating.

FIG. 2 is a schematic view of a structure near the head and an operation state of the hard disk drive according to the present invention. As shown in FIG. 2, a slider 2 is fixed at the tip of a head arm 1 in the hard disk drive and a read/write element 5 which performs reproduction/writing of magnetic information is made at one end of the slider 2. Also, pads which control the attitude of the slider 2 by use of an air current flowing between the head and the disk are provided on the surface of the slider 2 and a wear resisting diamond-like carbon film 3 (for pads at the inflow side) or a diamond-like carbon film 4 (for a pad at the outflow side) is formed on each pad. FIG. 3 shows a relation between the position of the slider 2 and that of the surface 7 of the disk at operation of the hard disk drive, and a section near the read/write element 5. In FIG. 3, the slider 2 is arranged on the surface of the head arm 1 which is formed with SUS and the like and the read/write element 5 is provided on the surface near the tip part of the slider 2. And, the surface of the slider 2 including the surface of the read/write element 5 is covered with wear-resisting diamond-like carbon layers 4 through silicon layers 6. The material forming the above-described slider 2 was alumina. FIG. 3 shows a state that a floating type head which has a space between the head and the surface 7 of the disk is operated. Since the floating quantity is approximately 10 nm as a product and about 8 nm as a device under development, there is a possibility that the head comes into contact with the minutely uneven surface 7 of the disk and a foreign substance on the surface 7, or collides with the disk due to an unstable attitude at start/end of the operation. Moreover, a contact type head under developing is operated in a state that the head and the disk come into contact with each other at any time. When the diamond-like carbon film 4 (the pad at the outflow side) provided on the slider 2 is gradually worn by the above contact or collision during operation and the read/write element 5 is finally exposed and oxidized, the hard disk drive becomes inoperative. In the hard disk head of this example, the film thickness of this diamond-like carbon film 4 (pad at the outflow side) was 6 nm and the thickness of the silicon layer 6 which improves the adhesiveness between the above film and the slider 2 was 2 nm. The quantities of wear were measured for the above films after sliding tests were conducted for one month under acceleration conditions.

FIG. 4 shows an analysis example of the Auger electron spectroscopy according to the example of the present invention and examples of changes in the energy spectrum of charged particles due to quantities of wear. FIG. 4A shows the Auger electronic spectrum which indicates that Si in the silicon layer 6, and Al, Ti, and O included in the slider 2 are detected through the thinned diamond-like carbon film 4 (hereinafter, abbreviated as "DLC film"). The horizontal axis indicates the kinetic energy of electrons and the vertical one expresses the number of detected electrons. Auger electronic peaks belonging to C, Si, Al, Ti, and O are recognized over a large back ground in FIG. 4A. FIG. 4B shows the changes in the Auger electron spectrums due to the quantities of wear. It is found that the energy spectrums of the charged particles which have been superimposed become larger in the rising order with regard to the quantities of wear, the peak intensity of Si is increased as the quantity of the wear is increased, and the intensity is reduced when detection of Al of the base layer is started.

FIG. 5 shows examples of the signal intensities and those of depth-direction distributions of the signal intensity ratios of the reference sample according to the present invention. FIG. 5A shows results in which the depth-direction distributions of the signal intensities for elements of C, O, and Si were measured, assuming that a head, which has been made in the same lot as that of the head which was subject to sliding tests for evaluation and has not been subject to sliding, was used for the reference sample. Peak heights in the energy spectrum of charged particles after smoothing was used in FIG. 5B according to the present example. Also, the sputter time (point A) equivalent to the interface between the DLC film and the silicon layer was set as 4.5 minutes, at which the maximum signal intensity of Si was obtained, by reasoning that it is objectively determined. FIG. 5B shows the depth-direction distributions of the intensity ratios for each element, which has been made, using FIG. 5A. The horizontal axis indicates the quantities of wear after conversion from the sputtered time in FIG. 5A. As described above, errors caused by differences in the film structures and fluctuations of the sputter etching rates may be suppressed by using the correspondence between the intensity ratios and the quantities of wear obtained from the reference sample with quite the same film structure as that of the measurement sample. Here, since the peak of Si is not detected as seen from the drawing when the quantity of the wear of the evaluation sample is equal to or less than 3.3 nm, it is required in such a case to perform sputter etching beforehand until Si is detected.

Figure 6:
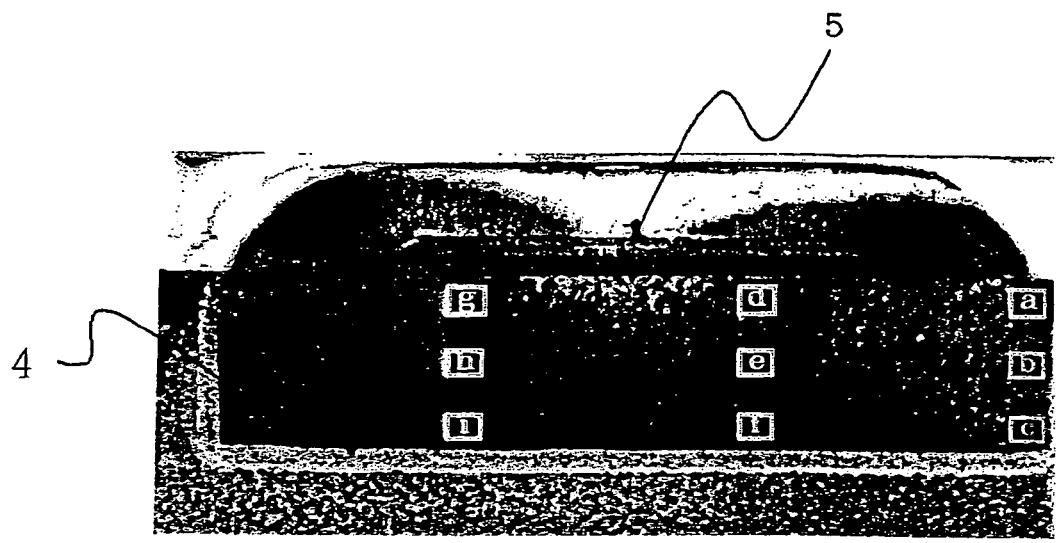
FIG. 6 is a view of an image picture of a scanning electron microscope indicating locations at which the quantities of wear according to the example of the present invention were measured.

FIG. 6 shows an image of a scanning electron microscope indicating locations at which the quantities of wear according to the example of the present invention were measured and the quantities of wear which were obtained at the above locations. Since evaluated quantities of wear were too small to detect Si under the above circumstances when the quantities of wear at nine points a through i shown in FIG. 6 were evaluated, the Auger electronic spectrum was measured after sputter etching was performed for approximately 2.5 minutes beforehand. Also, sputter etching of the diamond-like carbon film 3 at the inflow side, which had no possibility to come in contact with the disk, was simultaneously performed too and a reference point on the pad at the inflow side with no wear was used as a standard of zero for the quantity of wear.

Table 1 shows the quantities of wear at the above measurement points obtained by the above method. The above table includes the signal intensity ratios at the above-described measurement points and the quantities of wear obtained by comparison of the above ratios with the depth-direction profile of the reference sample. The apparent quantities of wear which were obtained just after sputter etching and the real quantities of wear before sputter etching which were obtained assuming that the quantity of wear at the reference point was zero are listed in the "apparent" column and the "real" one, respectively. It is found from the above table that the quantities of wear on the DLC film of the head depend on the locations, the maximum quantity is 2.5 nm, and not-even wear centered on the right side of the head in the image shown in FIG. 6 is generated.

TABLE 1

FROM INCORPORATED PRIORITY JAPANESE PATENT APPLICATION NO. 2002-111785, FILED ON Apr. 15, 2002

| Measurement points | Signal intensity ratios | | Quantities of wear [nm] | |
|---|---|---|---|---|
| | Si/C (×10) | O/C | apparent | real |
| point a | 5.56 | 0.25 | 5.9 | 2.5 |
| point b | 3.18 | 0.25 | 5.5 | 2.1 |
| point c | 2.11 | 0.07 | 5.0 | 1.6 |
| point d | 3.01 | 0.01 | 5.4 | 2.0 |
| point e | 1.54 | 0.02 | 4.7 | 1.3 |
| point f | 1.28 | 0.00 | 4.2 | 0.8 |
| point g | 1.2 | 0.00 | 4.6 | 1.2 |
| point h | 0.58 | 0.00 | 4.0 | 0.6 |
| point i | 0.31 | 0.00 | 3.6 | 0.2 |
| reference point | 0.22 | 0.00 | 3.4 | 0.0 |

As explained above, according to the present invention, very small quantity of wear of equal to or less than 1 nm on a sliding member with a thin protective film may be measured with high accuracy. Thereby, the prediction accuracy of the wear life for a protective film is improved and a testing period for prediction of wear life, for selection of the material of a protective film, and for determination of the shape of a sliding member can be remarkably reduced. Moreover, when the Auger electron spectroscopy which can analyze a very small area of equal to or less than 1 μm is used, differences in quantities of wear according to locations, that is, the presence of not-even wear may be easily judged by measuring the quantities of wear for a plurality of locations on a wear surface.

What is claimed is:

1. A wear measurement method by which a quantity of wear on the surface of a measurement sample formed with a surface layer on a base material is measured, comprising:
a reference-sample detection step of repeatedly recording a ratio between a signal intensity caused by an element in a base layer of the reference sample and a signal intensity caused by an element in the surface layer of the reference sample, which are obtained by etching a reference sample with the same layer structure as that of the measurement sample before substantial wear in the direction of the film thickness for preliminary wear and by applying excited ionization radiation on the reference sample during being etched and by detecting charged particles generated from the reference sample, and obtaining a relation between the quantities of preliminary wear and the ratios of the reference sample;
a measurement-sample detection step of detecting ratios between signal intensities caused by elements in the base layer of the measurement sample and signal intensities caused by elements in the surface layer of the measurement sample, which are obtained by applying the excited ionization radiation on the measurement sample after surface wear and by detecting charged particles generated from the measurement sample; and
a step of obtaining positional information on the surface of the measurement sample after wear by comparing the relation obtained in the reference sample detection step with the ratios detected in the measurement sample detection step.

2. The wear measurement method according to claim 1, wherein the surface layer is made of diamond-like carbon.

3. The wear measurement method according to claim 1, wherein the measurement sample is a read/write head of a hard disk drive.

4. The wear measurement method according to claim 1, wherein the etching is executed, using a sputter etching method.

5. The wear measurement method according to claim 1, wherein the surface of the measurement sample after wear is etched to a predetermined depth in advance before the measurement-sample detection step.

6. The wear measurement method according to claim 1, wherein the measurement sample has a wear area and a non-wear area, the method further comprising:
a step of etching the wear area and the non-wear area in the direction of the film thickness to be subject to preliminary wear before the wear measurement steps,
wherein the measurement-sample detection step respectively measures ratios between signal intensities caused by elements in the base layer of the measurement sample and signal intensities caused by elements in the surface layer of the reference sample, which are obtained by applying the excited ionization radiation on the wear area and the non-wear area after etching and by detecting charged particles generated from the measurement sample, and
obtains apparent quantities of wear for the wear area and the non-wear area by comparing the relation with the ratios, which are obtained in the reference sample detection step, and obtains a quantity of wear for the wear area of the measurement sample from the difference between the apparent quantities of wear.

7. A wear measurement method for measuring a wear surface layer of a measurement sample comprising a base layer, an intermediate layer formed on the surface of the base layer, and a surface layer formed on the surface of the intermediate layer, comprising:
a reference-sample detection step of repeatedly recording a ratio between a signal intensity caused by an element in the intermediate layer of the reference sample and a signal intensity caused by an element in the surface layer of the reference sample and a ratio between a signal intensity caused by an element in the base layer of the reference sample and a signal intensity caused by an element in the intermediate layer of the reference sample, which are obtained by etching a reference sample with the same layer structure as that of the measurement sample before substantial wear in the direction of the film thickness of preliminary wear and by applying excited ionization radiation on the reference sample during being etched and by detecting charged particles generated from the reference sample, and obtaining a relation between the quantities of preliminary wear and the ratios of the reference sample;
a measurement-sample detection step of detecting ratios between signal intensities caused by elements in the intermediate layer of the measurement sample and signal intensities caused by element in the surface layer of the measurement sample and ratios between signal intensities caused by elements in the base layer of the measurement sample and signal intensities caused by elements in the intermediate layer of the measurement sample, which are obtained by applying the excited ionization radiation on the measurement sample after surface wear and by detecting charged particles generated from the measurement sample; and
a step of obtaining positional information on the surface of the measurement sample after wear by comparing the relation obtained in the reference sample detection with the ratios among three elements detected in the measurement sample detection step.

8. The wear measurement method according to claim 7, wherein the surface layer is made of diamond-like carbon, and the intermediate layer is made of silicon.

9. The wear measurement method according to claim 7, wherein the measurement sample is a read/write head of a hard disk drive.

10. The wear measurement method according to claim 7, wherein the etching is executed using a sputter etching method.

11. The wear measurement method according to claim 7, wherein the surface of the measurement sample after wear is etched to a predetermined depth in advance before the measurement sample detection step.

12. The wear measurement method according to claim 7, wherein the measurement sample has a wear area and a non-wear area, the method further comprising:
a step of etching the wear area and the non-wear area in the direction of the film thickness to be subject to preliminary wear before the wear measurement steps,
wherein the measurement-sample detection step measures respectively ratios between signal intensities caused by elements in the base layer of the measurement sample and signal intensities caused by elements in the surface layer of the reference sample, which are obtained by applying the excited ionization radiation on the wear area and the non-wear area after etching and by detecting charged particles generated from the measurement sample;
obtains apparent quantities of wear for the wear area and the non-wear area by comparing the relation with the ratios, which are obtained in the reference-sample detection step, and obtains a quantity of wear for the wear area of the measurement sample from the difference between the apparent quantities of wear.

13. A wear measurement device, comprising:

charged particle measurement means for applying excited ionization radiation on a sample and measuring charged particles generated from the surface of the sample;

means for making an energy spectrum of the charged particles based on an output signal from the charged particle measurement means;

means for calculating signal intensities of plural elements forming the sample from the energy spectrum of the charged particles and calculating signal intensity ratios from the signal intensities of the plural elements;

means for making and recording calibration curves indicating relations between the signal intensity ratios of the plural elements and depth-positional information on the sample for which the energy spectrum of charged particles has been observed;

means for measuring values of the signal intensity ratios of the plural elements calculated from the energy spectrum of charged particles for the measurement sample; and means for calculating the quantity of wear for the measurement sample from the values of the signal intensity ratios of the plural elements for the measurement sample and data of the calibration curves.

14. The wear measurement device according to claim 13, wherein the means for calculating signal intensity ratios from the signal intensities of the plural elements, the means for making and recording the calibration curves, and the means for calculating the quantity of wear for the measurement sample are realized by a program contained in a single small processor.

* * * * *